United States Patent [19]

Wasileski

[11] Patent Number: 4,840,900
[45] Date of Patent: Jun. 20, 1989

[54] CONTINUOUS PROCESS FOR THE PREPARATION OF IMMOBILIZED GLUCOAMYLASE

[75] Inventor: John M. Wasileski, Brookfield, Wis.

[73] Assignee: National Distillers and Chemical Corporation, New York, N.Y.

[21] Appl. No.: 37,652

[22] Filed: Apr. 13, 1987

[51] Int. Cl.$^4$ .................. C12P 19/20; C12N 11/02; C12N 11/08; C12N 9/34

[52] U.S. Cl. ................................ 435/96; 435/177; 435/180; 435/205

[58] Field of Search ............... 435/96, 205, 174, 176, 435/177, 180, 182

[56] References Cited

U.S. PATENT DOCUMENTS 3,791,927  2/1974  Forgione et al. ............... 435/182
4,205,127  5/1980  Fujita et al. .................. 435/180 A

FOREIGN PATENT DOCUMENTS 2129806  5/1984  United Kingdom ............... 435/96

Primary Examiner—David M. Naff
Attorney, Agent, or Firm—Kenneth D. Tremain

[57] ABSTRACT

A continuous process for the preparation of immobilized glucoamylase useful for the long term continuous direct hydrolysis of starch to fermentable glucose at temperatures of 45° or higher is carried out by continuously depositing and stabilizing glucoamylase on a porous, particulate, macroreticular anionic ion exchange resin having a high osmotic shock resistance value. Processes for detoxifying, stripping and regenerating the biocatalyst are also disclosed.

16 Claims, No Drawings

CONTINUOUS PROCESS FOR THE PREPARATION OF IMMOBILIZED GLUCOAMYLASE

BACKGROUND OF THE INVENTION

1. Field of the Invention

The present invention relates to a continuous process for the manufacture of an immobilized biocatalyst which is glucoamylase immobilized on an ion exchange resin. The present invention also includes processes for stabilizing and detoxifying such biocatalyst and a process for stripping and regenerating such biocatalyst.

2. Description of the Prior Art

Starch has, previously, been saccharified biocatalytically with glucoamylase supported on various types of supports. French Patent 2372653 discloses the deposition of fungal derived glucoamylase on a macroreticular styrene-divinyl benzene anionic exchange resin and the use of the resulting material to saccharify solutions of starch at 10°–50° C. and preferably at 40° C.

The process used in this French Patent to load the glucoamylase onto the resin support, however, is a relatively inefficient batch process. Relatively large quantities of enzyme are used in this process, with less than about half of it absorbed on the resin, and with the excess enzyme being washed off and discarded. The batch enzyme loading procedure of the French Patent is also a relatively complex multi-step process that requires the use of buffering and resin filtering steps prior to the contact of the enzyme with the resin. The batch loading conditions of the French Patent process, of 12 hours at 4° C., thus require a relatively long process, and which would also require the use of refrigeration conditions which are relatively expensive to maintain. The batch loading process of the French Patent also has a very low loading efficiency of about 33%, and produces biocatalysts of relatively lower activity. A further, and very serious, disadvantage of the batch loading process of the French Patent is that of the need for repeatedly washing the resin with a buffered solution and under agitation for an extended period of time after loading the enzyme thereon. This washing procedure leads to the loss of additional enzyme from the resin and results in the creation of fines due to the attrition of the resin particles.

Prior to the present invention, therefore, it was not possible to readily and efficiently provide high loadings of glycoamylase on macroreticular anionic exchange resins.

An object of the present invention, therefore, is to provide a simple, economic and efficient process for readily providing biocatalysts comprising high loadings of glycoamylase on macroreticular anionic exchange resins.

A further object of the present invention is to provide a means for readily loading such enzyme on such resins in a stable and irreversible form.

A further object of the present invention is to provide a facile process for disinfecting said biocatalysts without significantly adversely affecting the enzymatic activity thereof.

A further object of the present invention is to provide a facile process for the rapid removal from such biocatalysts of any microbial inhibitors present in the resin and/or enzyme components thereof, without significantly adversely affecting the enzymatic activity of such biocatalysts.

A still further object of the present invention is to provide a facile process for stripping and regenerating such biocatalyst when in spent form.

SUMMARY OF THE INVENTION

It has now been found that the objects of the present invention can be achieved by employing, as a biocatalyst for the saccharification of starch, one prepared by fixing and stabilizing, as described below, the glucoamylase on certain macrorecticular anionic exchange resins and then detoxifying and disinfecting the resulting biocatalyst prior to its use to saccharify relatively concentrated solutions of liquified starch at temperatures of $\geq 45°$ C. over prolonged periods of time $\geq 6$ months. The spent biocatalyst may also be readily stripped and regenerated, as described below.

DESCRIPTION OF THE PREFERRED EMBODIMENT

Glucoamylase

The glucoamylase (or amyloglucosidase) which is employed in the biocatalysts of the present invention, may be any such water soluble enzyme material that will biocatalytically hydrolyze starch in an aqueous medium to D-glucose. The preferred glucoamylase materials are those that are derived from fungi, most preferably from strains of *Aspergillus* such as *Aspergillus niger* or *Aspergillus awamori*. Such a derived strain of glucoamylase was used in the Examples disclosed below.

The glucoamylase is preferably used in the form of an aqueous solution having an enzyme concentration of about 40 to 200 IU per milliliter (ml).

Anionic Exchange Resin

The anionic exchange resins that may be used as the carrier or support for the enzyme are basic, macroreticular, anionic exchange resins. They have a high degree of fixed porosity. They are particulate materials, preferably, having an average particle size of about $0.50 \pm 0.20$ mm. They may be strongly or weakly basic in nature.

The strongly basic anion exchange resins preferably have a quaternary ammonium functionality and preferably have a chloride ionic form. During conversion of these strongly basic ion exchange resins ($Cl^-$ to $OH^-$) they undergo a reversible swelling level of about 3 to 20% and more preferably of about 15–20%.

The weakly basic anion exchange resins preferably have a tertiary amine functionality and preferably have a free basic ionic form. During conversion of these weakly basic ion exchange resins (free base$^-$ to $Cl^-$) they undergo a reversible swelling level of about 15–28%.

These materials would have an ion exchange capacity of about 15–30 Kg $CaCO_3/ft^3$. They have a moisture content of about 55–60% as shipped by the manufacturer. The most preferred of such anion exchange resins are those prepared from crosslinked styrene-divinyl benzene resins. Rohm & Haas Co. of Philadelphia NJ USA markets a class of such resins under the trademark Amberlite.

For use in the present invention the ion exchange resins are, preferably, first washed with water to remove therefrom any fines and extractables present therein.

The most preferred of such resins is that sold by Rohm & Haas company under the trademark Amberlite anionic resin IRA 94 which has a tertiary amine functionality, a pore size in the order of about 900 to 2000 Angstrom units, is in free base anion form, has a swelling capacity of 15–20%, is weakly basic, has a moisture content of 60% and an ion exchange capacity of 26.2 kilograms $CaCO_3/ft^3$ and has been chemically treated to proide osmotic shock resistance. It has a bulk density (wet) of 0.64 gms/cc and a true density (dry) of 1.05 gms/cc.

Immobilized Biocatalysts

When made according to the process of the present invention, the immobilized enzyme biocatalysts have what may be termed, and with respect to the starch solutions in which they are used as biocatalysts, as well as with respect to the carbohydrate solutions in which they are stabilized, as described below, a settling density. That is, these particulate biocatalysts will readily sink below the surface of such solutions having a density <1.2 g/ml and sink to the bottom of the container in which such solutions are contained, and will not float on the surface thereof. This allows the solutions in which the biocatalysts are used to be readily separated therefrom by gravity.

Starch

The starch which is treated with the biocatalysts prepared by the process of the present invention is used in the form of a liquified starch. The liquified starch is prepared, usually, by cooking starch at a temperature of about 100°±20 C. in the presence of acid or an endoenzyme such as alpha amylase, or a sequential combination of both of such materials. The liquified starch is used at a solids concentration of about 10 to 50, and preferably of about 20 to 45 weight %. The starch may be derived from any of the commonly available sources thereof such as cereal grains, manioc (cassava) roots and potato tubers. The preferred source is cereal grain and the most preferred source is corn.

The liquified starch also, preferably, has a salt (inorganic and organic ions) content of 0 to ≦6%, and preferably of 0 to ≦1%, by weight and an insoluble solids content of about 0 to 2%, and preferably of about 0 to ≦1%, by weight and a density of about 1.04 to 1.20 g/ml. It has an organic acid content of ≦1%.

A preferred form of such liquified starch is a highly purified cornstarch called maltodextrin. This material is an acid/enzyme liquefied starch that is water soluble but not hygroscopic. A comparison of the saccharification of maltodextrin versus liquefied clarified cornstarch showed identical kinetics in both batch and continuous operations when each type of starch was taken to the same D.E. in liquefaction. By high purity in this regard it is meant >99% on a dry basis.

D.E. or dextrose equivalent, which is a measure of average polysaccharide length, is a more important starch hydrolysis rate determinant than the pretreatment given to the cornstarch. In solution, mashes of low D.E. (long polymeric chains) saccharify more completely than high D.E. mashes at equivalent conditions, but in the immobilized glucoamylase column reactor, it is just the opposite suggesting that the largest dextrin molecules have difficulty diffusing into the resin proes. For example, continuous saccharification using immobilized glucoamylase in a column reactor at 45° C. and a 0.68 hour residence time showed 86 and 89–90% conversion of 22 weight % M-100 (D.E.=10) and M-200 (D.E=20) maltodextrin, respectively. These maltodextrins are produced by Grain Processing Corporation and sold under the tradename Maltrin. The preferred corn grit mashes are taken to a D.E. of 20 to achieve good clarification and carbohydrate yield. Mashes having a D.E. of 10 to 30, and preferably of 10 to 20, are preferred.

Biocatalyst

The biocatalyst of the present invention is prepared in a continuous mode of depositing or fixing the enzyme on the washed support and then stabilizing the enzyme on the support, and finally detoxifying and disinfecting the supported enzyme.

The enzyme is thus fixed on the support by continuously pumping through the porous support a solution of the glucoamylase at such a rate as to provide for a liquid residence time of about 1–2 hours. The continuous absorbtion process is conducted at atmospheric pressure and at a temperature of about 25° to 45° C., and preferably not above 50° C., and at a pH of about 3.7 to 4.3.

The solution of enzyme used, preferably, has a dissolved enzyme content of about 100 to 200 IU/ml of such solution. The strength and volume of such solution are so regulated as to provide that the resin will absorb about 1000 to 1500 IU of enzyme per gram of support resin.

The enzyme solution is buffered to a pH of 4.0±0.3 with a salt of a weak acid and strong base, preferably 0.035±0.015M acetate buffer solution.

The more preferred mode of operating the process of the present invention involved in preparing the biocatalyst is as follows:

The process for preparing the biocatalyst, which latter material comprises glucoamylase immobilized on porous, particulate, macroreticular anionic exchange resin, wherein the glucoamylase is a water soluble fungal derived enzyme, and the resin is in free base form and has a particle size of about 0.50±0.20 mm, and the particles thereof have pore sizes therein of about 900 to 2000 Angstrom units, comprises depositing the enzyme on the resin in a continuous deposition mode of operation, with the depositing being carried out in a period of about 1 to 2 hours at a temperature not to exceed 50° C. with 10±5 volumes of enzyme solution per volume of the resin, the enzyme solution having a concentration of about 100 to 200 IU of enzyme per ml of the enzyme solution, and the enzyme solution being buffered with acetate buffer at a pH of 4.0±0.3, and the depositing thereby providing a loading of about 1000 to 1500 IU of the enzyme per gram of the resin in dry form.

Using the procedure and materials described above it is thus possible to readily achieve up to about a 95% efficiency in depositing the enzyme on the support at a liquid residence time of about 1 to 2 hours, when, preferably, employing an excess of the enzyme.

The deposited enzyme is then fixed on the support by treating (contacting) the deposited enzyme with an aqueous solution of carbohydrate selected from the group consisting of starch, glucose, oligosaccharides, dextrins and mixtures thereof. The contacting time required is about 1 to 2 hours at 25° C. to 50° C., depending on the strength of the carbohydrate solution used.

These solutions have carbohydrate concentrations of at least 1% and preferably of up to about 25–30% by weight. They have dissolved salt (organic and inorganic) concentrations of 0 to 1%, and undissolved solids contents of about 0 to 2%. The end point of the fixation process is obtained after treating a unit volume of the biocatalyst with about 5 to 10 volumes of the carbohydrate solution, in a continuous, rather than a batch, mode of operation.

The term stabilizing, as used with respect to this invention, means that the deposited enzyme is fixed within the pores of the anion exchange resin by contact with the carbohydrate (solution). It is believed that the enzyme attaches glucose moieties (glycosylates) to reach full activity, and so in effect, glucoamylase swells within the resin pores and either becomes physically entrapped, or is chemically so altered that even a challenge with other anions cannot displace the immobilized glucoamylase. To accomplish this desired entrapment of the enzyme, it has been found that the pores of the resin must be 900–2000 Å in size.

The biocatalyst is also preferably disinfected against microbial growth (thereon) during the hydrolysis process. The disinfectant of choice is a heat-labile or heat sensitive water soluble antibiotic, that is, an antibiotic that will eventually be destroyed during the hydrolysis process (which is conducted at $\geq 45°$ C.) and prior to the use of the glucose product in a subsequent fermentation process. The antibiotic should thus be one which is inactivated at temperatures of $\geq 45°$ C. The preferred of such antibiotics is nystatin. The antibiotic is used at disinfection effective levels, i.e., about 20 to 100 ppm.

The biocatalyst is also preferably detoxified by passing a liquified starch feed containing 6 weight % sodium sulfate through the biocatalyst bed at a residence time of one hour for a period of six hours followed by a salt-free liquified starch flush of seven hours. Alternatively, the salt containing feed can be pulse fed for one hour followed by a (1 hour soak) salt-free flush, the overall process being following three times to achieve complete detoxification.

In lieu of sodium sulfate, any other salt of a strong acid and base, in dilute solution form ($\sim$5–10%) can be used as a detoxifying agent for the purposes of the present invention. The use of the solutions of the detoxifying agent results in the flushing of the microbial inhibitors from the catalyst bed.

Chemicals for sterilization of the biocatalyst can be added during this detoxification step, as the reaction effluent during this period cannot be fermented.

Hydrolysis of the Starch

The starch is biocatalytically hydrolyzed enzymatically to D-glucose by contacting the liquified starch with the immobilized glucoamylase biocatalyst. The hydrolysis reaction is preferably conducted continuously, but may also be conducted semicontinuously or in a batch process.

The hydrolysis reaction may be conducted at temperatures of about 10° to 60° C., but is preferably conducted at about 45° to 55° C. The glucoamylase is more active at the higher temperatures, and at such temperature the bioreactor is less susceptible to microbial contamination. At temperatures of below 45° C. microbial contamination may become a major problem if other steps are not taken to curtail such contamination. When used at the higher ($>45°$ C.) temperatures, however, the active life of the biocatalyst diminishes, although the percent conversion increases somewhat from about 90% to about 95% as the temperature is raised from about 45° C. to about 50° C. These percent conversion values were obtained in studies employing a 22 weight % maltodextrin feed at a 0.75 hour residence time.

The hydrolysis is preferably conducted at a pH of $4.0 \pm 0.3$. To mantan such pH range the starch solution being hydrolyzed is buffered with a 0.02–0.05M acetate buffer solution, and preferably one having a molar ratio of 2 to 3, & preferably $2.5 \pm 0.3$, of acetic acid to sodium acetate.

The glucose product that is directly produced by the use of the immobilized enzyme biocatalyst of the present invention is a fermentation grade of glucose. That is, it can be used directly in any fermentation process, including one designed to produce ethanol from glucose, without further purification or treatment of the glucose solution except for appropriate dilution.

During the use of the biocatalyst of the present invention in the hydrolysis of the starch materials to glucose, it has been found that the biocatalyst is extremely resistant to organic fouling. By that it is meant that unconverted carbohydrates and/or entrained oils and solids are not retained by the biocatalyst.

The Bioreactor

The bioreactor to be used in the hydrolysis process may be a stirred tank, an expanded bed reactor or a packed column reactor, with the expanded bed reactor being preferred. The expanded bed may or may not be fluidized. The stirred tank reactors are closed vessels with centrally or axially positioned impellers and may be used for continuous processes. Any of these reactors can be used with clarified starch solutions having a starch concentrations of about 10 to 55 weight %.

Immobilized glucoamylase biocatalyst can also be used in column reactors. These reactors can be operated in either an upflow (expanded) or downflow mode. There are advantages to operating in either mode. In the expanded mode, starch hydrolysates do not have to be completely clarified before saccharification, as the particulate material can migrate through the expanded resin bed. In the downflow mode the resin bed tends to behave as a filter and starch hydrolysates must be much more clarified for the system to function properly. The greater relative biocatalyst concentration in the downflow mode of operation does result in a higher unit productivity however.

Repeated experiments have shown that 625 g of virgin IRA 94 resin produces one liter of packed bed of enzyme-loaded equilibrated resin. Since the moisture content of shipped resin is 60%, this corresponds to 0.25 g resin/ml of bed. Thus in an unexpanded bed reactor the aqueous phase comprises about 75% of the reactor volume. In calculating residence times for column reactors, the value is corrected (25%) for the inert (solid) volume in the reactor. Due to density contributions of concentrated glucoamylase enzyme and assorted salts, the apparent density of the immobilized biocatalyst is 1.2 g/ml. Thus the biocatalyst can be used in upflow (expanded) column operations with feeds having an apparent density of <1.2 g/ml, and preferably a starch concentration of <35 weight %.

In continuous operations, in the stirred tank or in the column reactor types of bioreactors, the starch solution being hydrolyzed is passed through the biocatalyst resin bed in the reactor at the rate of about 1 0.3 reactor volumes/hour. This correspondingly provides a residence or retention time for the solution of about 0.75 to 4 hours.

The reactors employed in the Examples disclosed herein are bench scale laboratory reactors.

Residence or retention time means the time required to replace or turnover the aqueous volume of the biocatalyst bed with a continuous feed of the aqueous solution being used at a given constant feed rate. Since the solid resin fills about 25% of the biocatalyst bed volume, the "real" residence time is 75% of the "superficial" residence time.

Regeneration of the Biocatalyst

After the biocatalyst has been in use for some time its strength or activity will become depleted, as noted below in the Examples. It has been found that this biocatalyst can be readily restored to 100% activity, for long term ($\geq$1-2 years) reuse, by stripping the used enzyme from the resin support and then recharging the thus cleansed support with a new charge of enzyme as otherwise described above, or in the Examples below.

In order to accomplish the stripping of the glucoamylase enzyme from the support of the present invention on which it has been deposited and stabilized, as described above, however, it is necessary to use a specific stripping procedure. This stripping procedure requires that the enzyme charged resin be successively treated, first with an aqueous solution of strong acid and then with an aqueous solution of strong base. After each washing or rinsing of the biocatalyst with acid or base it is washed or rinsed with water prior to the onset of the next washing with acid or base, or the deposition of the fresh enzyme charge. The sequence of use of the acid and base washings need only be done once or may be conducted about 2-3 times in order to assure complete removal of the depleted enzyme. The washings are done at 25° C. The strong acid to be used would include sulfuric acid. The acids would be used in aqueous solutions thereof having an acid concentration of about 2 to 10 weight %.

The strong base to be used would include sodium hydroxide. The bases would be used in aqueous solutions thereof having a base concentration of about 2 to 10 weight %.

Each acid or base washing would take about 5 to 10 volumes of wash per volume of spent biocatalyst being treated.

The following examples are merely illustrative of the present invention and are not intended as a limitation upon the scope thereof.

EXAMPLE 1

Loading of Glucoamylase on Resin

The glucoamylase enzymes described above bind readily to the macroreticular anion exchange Amberlite resin IRA 94. In a commercial application, the enzyme must be loaded in such a fashion that the maximum amount of the enzyme applied to the resin is immobilized, and that the resulting supported biocatalyst has attained maximum activity. To accomplish this it has been found that the enzyme must be applied to the resin continuously rather than in a batchwise fashion.

The batch glucoamylase loading process (wherein a high concentration of the enzyme is added to the anion exchange resin and mixed gently) is a more rapid loading method than the continuous loading process relative to the amounts of enzyme that can be loaded by such batch process. However, in order to achieve whatever loadings are possible in the batch process one must still contend with the main drawback with batch enzyme loading in that a substantial percentage of the enzyme used in the loading solution is not bound even with prolonged incubation. There is thus essentially no difference in the amount of enzyme bound or absorbed between mixtures of enzyme and resin that were incubated over a period of one hour as well as over a period of 18 hours when using a batching loading process. The following results were obtained in a one hour batch loading experiment with IRA 94 resin:

| Initial Glucoamylase Concentration (IU/ml) | Glucoamylase Bound IU/g resin | Efficiency (% Bound) |
|---|---|---|
| 10 | 43 | 42 |
| 10 × 2 | 66 | 33 |
| 100 | 412 | 41 |
| 100 × 2 | 552 | 27 |
| 200 | 607 | 29 |
| 500 | 580 | 11 |

This experiment indicated that more than 100 International Enzyme Units per ml (1 I.U.=amount of enzyme required to release 1 micromole glucose per minute from 1 weight % soluble starch at pH 4 and 37° C.) of glucoamylase is required to fully charge the resin in a batch loading process. Higher glucoamylase concentrations result in excess unbound glucoamylase and lower concentrations do not provide sufficient driving force to achieved maximum loading. If the loading cycle is repeated (indicated by the "x2" designation), the amount of bound glucoamylase is increased due to the higher driving force of the second cycle, but the % efficiency, relative to the total amount of enzyme used, is significantly decreased. If extended, this concept results in the continuous application of a dilute enzyme stream to the resin support. This loading approach is more applicable if the support is used in a tubular plug-flow loading reactor.

The continuous application of glucoamylase enzyme to the resin support, however, in accordance with the present invention, is very efficient in terms of the percentage of available enzyme which is bound to the support, although this method does take considerably longer than the batch procedure for equivalent enzyme loading. This is due to the smaller "driving force" for enzyme adsorption at the low glucoamylase concentration used in the continuous loading procedure. Repeated experiments with the continuous loading process have shown that a glucoamylase concentration of about 100 IU/ml is sufficient to enzymatically charge a column reactor packed with IRA 94 resin. When applied continuously up to 95% of the enzyme can be immobilized on the resin. This compares to only about 42% binding efficiency in the best batch system. The resin support (IRA 94) will absorb 375 IU per ml of packed bed. Typically, a 25% excess (500 IU/ml resin) of the enzyme is used to insure maximum biocatalyst loading. A one hour residence time for the enzyme feed is recommended so that enzymatically charging the column usually takes about 1 to 2 hours per foot of column height. Feeding enzyme faster will probably reduce enzyme binding efficiency as the reaction is diffusion limited. Elevated reactor temperatures are not required during glucoamylase loading but increasing reactor temperature to 45° C. helps minimize microbial contamination. The enzyme feed is prepared by suspending the glucoamylase in acetate buffer (0.05M, pH 4.3). The acetate buffer is prepared by diluting 26.5 ml of 0.5M sodium acetate and 73.5 ml of 0.5 acetic acid to one liter.

During enzyme adsorption there is an exchange of hydroxide ions so the effluent pH is initially about 4 pH units higher than the influent. As the capacity of the bed is approached, the pH of the effluent drops to match that of the feed and the bed undergoes an 18 percent expansion in volume. No other physical changes are evident in the resin bed.

EXAMPLE 2

Fixation of Glucoamylase on Resin

After adsorption onto the resin (with pore size of 900–2000 Å), the enzyme is loosely bound and can be readily removed by displacing the enzyme with other anions. However, if the biocatalyst is first exposed to a low ionic strength starch substrate the enzyme becomes fixed in place and cannot be removed even in the presence of 6% sodium sulfate. The stabilization phenomenon was discovered when it was noted that a 2 weight % solution of sodium chloride could displace 93% of bound glucoamylase if applied immediately after enzyme attachment. After incubation for 3 days in a 10 weight % starch solution, at 45° C., however, no enzyme was released by the sodium chloride treatment. In Table I below a variety of glucoamylase loading sequences and the effect on subsequent saccharification and fermentation is shown. Regardless of whether the resin is charged batchwise or continuously, the biocatalyst must be stabilized for about 1 to 3, preferably about 2, hours in a starch medium before exposure to solutions containing high concentrations of salt. This stabilizing phenomenon is important in the commercialization of this process since the commercially used water is likely to contain high concentrations of anions. It would also be important when considering a detoxification step as described below. The stabilization step need not be a continuous process as we have demonstrated that this phenomenon occurs in batch operations as well.

EXAMPLE 3

Enzyme Fixation and Detoxification of the Biocatalyst

A problem that was encountered in preparing the immobilized catalyst was that in the industrial production of anion exchange resins there are usually residual chemicals remaining in the resin which are called "extractables". In the case of the macroreticular Amberlite resins, these are primarily divinyl benzene-styrene dimers and trimers. Although the resin may be washed by the manufacturer before shipping and is rinsed again prior to use in an immobilized glucoamylase system, these materials leach out into the product stream during operation and inhibit subsequent microbial fermentation. The IRA 94 resin undergoes a reversible expansion or contraction (20%) depending on the ionic form of the resin. If the resin is in the sulfate (expanded) form the extractable are rapidly and easily leached from the resin. The glucoamylase does not bind tightly to the resin in the expanded form however (Table I). Thus the enzyme must be loaded and fixed in place prior to resin expansion to release the extractables. The expansion occurs slowly and naturally during normal operation of the starch hydrolysis process or it can be accelerated by applying a high concentration of sulfate ions to the biocatalyst after enzyme stabilization. The method that works the most rapidly and produces the smallest amount of waste material is to pulse feed a dextrin feed containing 6 weight % sodium sulfate through the biocatalyst bed. This solution is fed at a rate such as to turn over about 2 volumes of reactor per hour and then the pump is turned off and the bed allowed to soak for 1 hour. After 3 such cycles the extractables are completely flushed from the bioreactor (Table I). Chemicals for disinfectionn of the biocatalyst can be added during the detoxification step as the reactor effluent during this period is not usually fermented. The extractables absorb light in the ultraviolet wavelength, so that by tracking the U.V. absorption characteristics of the column effluent, the effectiveness of the detoxification procedures can be monitored. Following this treatment, an easily fermentable glucose stream is available after about 7 hours operation (Table I).

The detoxification can be performed prior to loading the glucoamylase on the resin. However, when this is done the resin must then be reconverted to the free base form and washed before loading the glucoamylase as described in Example 9 below.

Another problem was that, typically, commercial enzyme manufacturers add microbial inhibitors to their products to extend the shelf life of these materials. Benzoic acid and sorbic acid are examples of commonly used additives. Normally the enzyme solutions are diluted to such an extent in use that the microbial inhibitors are not a factor. A concentrated glucoamylase stream is used, however, to prepare the immobilized biocatalyst of the present invention. If special procedures are not followed to lower the concentration of these microbial inhibitors to 2 ppm, these inhibitors may inhibit subsequent fermentation of the glucose product. If the above procedure for releasing "extractables" from the resin is followed, however, the microbial inhibitorss contributed by the enzyme solution are released from the biocatalyst along with the "extractables" from the resin. The toxic effects of microbial inhibitors in the enzyme solution are far less than the "extractables". Thus after biocatalyst regeneration it may be more economical to blend the initial glucose product obtained therewith with purer glucose material obtained from other immobilized bioreactors.

TABLE I

| | INITIAL GLUCOAMYLASE LOADING PROCEDURES | | | | | |
|---|---|---|---|---|---|---|
| Level of | Procedures | | Conversion (3) | | Fermentation (4) | |
| Enzyme Loading | Stabilization (1) | Detoxification (2) | Day 1 | Day 7 | Flush | Metabolism |
| 100 IU/ml RT = 1 hour | 4 hours RT = 1 hour | 7 hours RT = 1 hour | 94 | 93 | 24 hour | Rapid |
| 100 IU/ml RT = 1 hour | 1 hour RT = 1 hour | 16 hours Batch | 86 | 85 | ND | ND |
| 400 IU/ml Batch | 0.75 hour RT = 1 hour | 3 hours RT = 1 hour | 70 | 68 | ND | ND |
| 400 IU/ml RT = 1 hour | 5 hours RT = 1 hour | 6 hours RT = 1 hour | 91 | 93 | 7 hours | Rapid |
| 400 IU/ml | 2 hours | 3 × 1 hour | 93 | 93 | 4 hour | Slow |

TABLE I-continued

| | INITIAL GLUCOAMYLASE LOADING PROCEDURES | | | | | |
|---|---|---|---|---|---|---|
| Level of | Procedures | | Conversion (3) | | Fermentation (4) | |
| Enzyme Loading | Stabilization (1) | Detoxification (2) | Day 1 | Day 7 | Flush | Metabolism |
| RT = 1 hour | RT = 1 hour | pulses feed 1 hour soak 1 hour | | | 12 hour | Rapid |
| 400 IU/ml Batch | 2 hours RT = 0.5 hour | 3 × 1 hour pulses | 88 | 83 | ND | ND |
| 400 IU/ml RT = 1 hour | — | 2.5 hours Done before Enzyme loading | 94 | 89 | ND | ND |

Flush = Hours after start-up before collecting sample for fermentation.
RT = residence time during continuous operation
ND = not determined
(1) Stabilizaiton of loaded enzyme by treatment (incubation) at 45° in 10 weight % starch solution for period of time indicated.
(2) Continuous or pulse feed of an aqueous solution containing 10 weight % dextrin and 6 weight % sodium sulfate at 45° through the bed of stabilized biocatalyst for indicated periods of time.
(3) Conversion results obtained when detoxified stabilized biocatalyst is used ot hydrolyze a 10 weight % solution of maltodextrin for 1 or 7 days at 45°.
(4) The fermentation conditions employed to demonstrate the level of contaminants present in the glucose products obtained from the detoxified stabilized biocatalysts were the following:
Flask fermentation with 1 ml of 50 g/l Y of a S. Cervisiae strain of yeast 16 weight % glucose + 5 weight % ETOH stress Buffer, nutrients, minerals and vitamins at 32° C.
The results indicate that the rate of metabolism of the glucose product by the yeast as measured by $CO_2$ evolution is not affected by the detoxification.
Rapid = faster than control during log phase
Slow = slower than control of growth cycle.

EXAMPLE 4

Disinfection of the Biocatalyst

Starch hydrolysates prepared directly from grain sources contain a number of nutritional components in addition to carbohydrates. Thus they make an excellent medium for microbial growth. Consequently, immobilized glucoamylase bioreactors are subject to microbial contamination. The operating temperatures of $\geq 45°$ C. are restrictive to microbial growth. Thus temperature is the primary barrier to microbial contamination. However, occasionally, thermotolerant microorganisms, particularly thermotolerant fungal strains, will proliferate, so a chemical method of disinfecting the immobilized biocatalyst is also needed.

A variety of purely chemical approaches were tested. These included pH shifts (acid or alkaline), solvents (ethanol, acetone, or chloroform), and iodine-based disinfectants (Microklene). These approaches were not suitable because the agents had to be used at such high concentrations that biocatalyst activity was affected. At lower concentrations, the cessation of microbial growth was only temporary.

Antibiotics were found to be the best alternative for disinfecting the biocatalyst. They are effective at low concentrations and do not interact with enzymes. Penicillin has proven effective at controlling bacteria that are present in commercial enzyme preparations. It can be added along with glucoamylase when charging the resin bed. Antibiotics are complex organic molecules which in some cases are unstable at elevated temperatures. A novel concept we have used, is to employ a temperature-sensitive antibiotic, for example nystatin, to kill fungal contaminants in our column bioreactors. The primary contaminant problem is at the reactor inlet where the effective concentration of nystatin is highest. As the antibiotic moves through the column it is gradually destroyed by the $\geq 45°$ C. operating temperature. If done properly, yeast can be grown directly on the column effluent while feeding the antibiotic to the bioreactor. The nystatin is preferably used at a concentration of 10 to 50 ppm.

EXAMPLE 5

A number of factors were shown to affect the relationship between flow rate and bed expansion. In particular, temperature and ionic equilibration of the anion exchange support resin are important.

The effect of flow rate (gallons per minute per square foot, gpm/sq.ft) on % bed expansion when operating upflow is a linear relationship, with the linear expression passing near the origin with a slope of 43.8 and an intercept at −1.95. A flow rate of 2.3 gpm/sq.ft. with 20 weight % maltodextrin feeds would be required to expand the bed 100%. The column reactor used for this study had been operated extensively before the bed expansion tests so the bed had ionically equilibrated. The temperature of the feed and the column itself were regulated at 45° C. The biocatalyst bed in this experiment was 3" in. I.D. by 12.9". A 3" I.D. by 59" column reactor was used for an expansion study and gave results which were similar. The feed for these experiments contained 20 weight % maltodextrins having a D.E. of 20 and a density of 1.09 gm/ml.

An immobilized glucoamylase column reactor was prepared and set up to run upflow. Feeds were prepared from a mixture of corn grits and meal using the liquefying enzyme alpha-amylase. The feeds were clarified with a sparkler filter. This clarification is similar to that achieved with rotary drum filters commonly used in the industry on a commercial scale. The clarified feeds had a salt content of 6 weight % and a starch content of 20 weight % and a D.E. of 20–25. The biocatalyst used was prepared as described above in Examples 1–4 using a continuous mode of depositing the enzyme on the resin and contained 1000–1500 IU of glucoamylase/-gram IRA 94 resin.

A 60 day continuous saccharification run was conducted using this system at 45° C. and pH of 4. No physical problems were observed during the run and starch conversion was typical for this type of reactor. Proteinaceous material present ($\sim \leq 1$ weight %) in the feed did not foul the biocatalyst and undissolved solids ($\sim \leq 1$ weight %) in the feed were able to pass through the resin bed. This experiment confirms that immobilized glucoamylase of the present invention in upflow column reactors can be used to saccharify marginally clarified feeds.

Bed expansion is also a function of the density of the liquid fed. Density is, in turn, a function of the carbohydrate concentration, so bed expansion varies with carbohydrate concentration as well as with flow rate. Data shown was with a feed of density 1.09 g/ml. A similar linear relationship of bed expansion to flow rate was also obtained at a feed density of 1.15 g/ml, but of differing slope.

EXAMPLE 6

A study of the effect of flow rate on starch conversion was completed in both the upflow and downflow column reactor orientations. In the upflow (expanded) mode, the conversion of starch is affected both adversely by the decreased enzyme concentration and positively by the increased residence time at a given flow rate. Only the aqueous volume of the reactor bed is used in the residence time calculations. The feed was a clarified maltodextrin solution (20% by weight dextrin and D.E. 20) which had a salt content of 1 weight %, and an undissolved solids content of 1 weight %.

The biocatalyst used was prepared as described above in Examples 1-4 using a continuous mode of depositing the enzyme on the resin, and contained 1000-1500 IU of glucoamylase/gram IRA 94 resin.

A series of feed flow rates were selected and run in the immobilized glucoamylase column in the downflow and upflow orientation. Starch conversion for each flow rate was determined along with bed expansion data for the upflow systems. The results are shown in Table II below. As shown there is essentially no difference in conversion between the upflow and downflow systems at any residence time greater than 0.5 hours. This is expected since the bed expansion at this flow rate (0.16 gm/sq.ft.) was less than 5% (based on the linear relation of % expansion vs flow rate discussed at above in Example 5). At higher flow rates (shorter residence times) conversion in the downflow system is slightly higher than in the upflow system (Table II). However, if the conversion ratio of the two operating modes are compared, the difference is slight even in the fastest (i.e. most expanded) system tested. The decrease in enzyme concentration in the expanded bed system is approximately compensated for by the increase in hydraulic residence time. The slight depression in conversion for the upflow systems may be due to diffusion effects and/or the heterogenic nature of the immobilized glucoamylase system. For the purpose of design, the concern over expansion effects on conversion can be largely ignored and one need only be concerned that residence time is sufficient to reach the desired degree of substrate conversion. Conversion rises rapidly with increasing residence time to about 93% at a 0.75 hour hydraulic residence time. Higher levels of substrate conversion can be obtained at longer residence times and it is an economic question as to whether or not a marginally increased conversion would justify the necessary increase in bed size.

The preferred residence times, therefore, are 0.75 to 2 hours.

TABLE II

Example 6 Reactions
EFFECT OF FLOW RATE ON SUBSTRATE CONVERSION

| Downflow | | Unflow | | Feed | Downflow/ |
|---|---|---|---|---|---|
| Residence Time (Hrs.) | Conversion (%) | Residence Time (Hrs.) | Conversion (%) | Flow Rate (gpm/sq ft) | Upflow Conversation rate |
| 0.06 | 39.9 | 0.15 | 36.0 | 1.48 | 1.11 |
| 0.12 | 57.7 | 0.19 | 54.2 | 0.74 | 1.06 |
| 0.18 | 67.9 | 0.25 | 65.0 | 0.49 | 1.04 |
| 0.37 | 81.3 | 0.43 | 74.8 | 0.25 | 1.09 |
| 0.56 | 88.5 | 0.58 | 90.8 | 0.16 | 0.97 |
| 0.76 | 91.3 | 0.75 | 93.2 | 0.12 | 0.98 |
| 1.12 | 93.2 | — | — | 0.08 | — |
| 1.50 | 94.4 | 1.46 | 93.8 | 0.06 | 1.01 |
| 2.39 | 97.0 | — | — | 0.04 | — |
| 3.08 | 98.1 | — | — | 0.03 | — |

Bioreactor conditions for Example 6.
Temperature = 45° C., Feed = 220 g dextrin/L = 240 g avail. glucose/L,
Superficial Reactor volume = 1450 ml.

EXAMPLE 7

A long range continuous saccharification run was set up to determine the stability, at 45° C., of immobilized glucoamylase biocatalyst made by the continuous deposition process of the present invention. The biocatalyst was prepared in a column reactor by fixing 1000-1500 IU/gram of glucoamylase (derived from Aspergillus niger) on Amberlite IRA 94 exchange resin, in a continuous mode of operation, from an aqueous solution containing about 100 IU/ml of the enzyme and having a pH of about 4.3 at a flow rate corresponding to a liquid residence time of 0.75 hours. The absorption or fixing process took about 5 hours. The Amberlite 94 IRA resin had previously been detoxified to $\leq 2$ ppm of extractibles.

The thus absorbed enzyme was then stabilized on the resin carrier by being treated (brought into contact), with a 22 weight % solution of clarified starch for 5 hours at 45° C. at a flow rate corresponding to a residence time of 0.75 hours and pH of 4.3±3.

The saccharification process was conducted in a column reactor in an upflow mode of operation using a biocatalyst bed that was 2" in internal diameter and 12.9" long. The feed employed was an aqueous solution containing 22 weight % by weight of maltodextrin (MALTRIN M-200, D.E.=20). The bioreactor was operated continuously for 70 days at a retention or residence time of 0.75 hours, at 45° C. and at a pH of about 4.0±0.3. The conversion rate was initially about 92%, after a start-up time of about 24 hours, and gradually declined to about 88% over the 70 day run.

EXAMPLE 8

A continuous saccharification run was conducted to demonstrate the feasibility of saccharifying corn grits that had been acid liquefied. A batch of corn grits was liquefied using SO$_2$ in the steam injection reactor of a pilot plant. The material was centrifuged with the lab centrifuge and the supernatant was fed upflow to an immobilized glucoamylase reactor at a 0.75 hour residence time. Conversion was consistently 93% during the one week run and no physical or mechanical problems were encountered with this substrate material.

A long range continuous saccharification run was then conducted to determine the potential for using an immobilized glucoamylase reactor to prepare glucose feeds from cornstarch for an integrated continuous ethanol fermentation. Feeds were prepared by liquefying a 5:1 mixture of corn grits and meal using an alpha-amylase enzyme. This mash is similar to that which would be produced in a commercial facility. The mash was then clarified using a sparkler filter. The mash was adjusted to a solids content of 30.5 weight % (theoretical maximum conversion=280 g glucose per liter).

Feeds were amended with glycerol (18.4 g/L), ammonium sulfate (38 g/L), succinate (1.8 g/L), lactate (14.9 g/L), calcium chloride (2.0 g/L), and a yeast nutrient mix. A corn mash, prepared in this way, should be typical of one produced in a commercial ethanol plant with recycle of stillage water This was a "worst case" experiment since the concentration of salts, residual nutrients, and congeners would probably be lower in the real situation.

The immobilized glucoamylase reactor was set up and operating temperature was adjusted to 45° C. with a 0.75 hour residence time. During a 60 day run the conversion decreased from about 93% to 89% during the run. This is a slower conversion decline than that shown during a 70 day run on "clean" maltodextrin feeds that was discussed earlier in Example 7 above. This indicates that salts present in corn mashes, in amounts of up to about 0.5 weight %, will not adversely affect reactor stability. Additionally, this long term run indicates that the protein present (about $\leq$ 1 weight %) in a cornstarch hydrolysate will not plug or adsorb to the anion exchange resin support to any appreciable degree. Thus this type of biocatalyst should be amenable to commercial corn processing plants.

The biocatalyst used in this Example 8 was prepared as described in Examples 1-4 above in a continuous mode of operation and contained 1000-1500 IU of glucoamylase/gram of IRA 94 resin.

EXAMPLE 9

Regeneration of the Immobilized Glucoamylase Biocatalyst

A question of key economic importance when considering an immobilized enzyme system is whether the biocatalyst can be renewed or regenerated once its catalytic ability has declined to unacceptable levels. In the process as described above, a fairly expensive enzyme (glucoamylase) has been immobilized onto an even more expensive support (IRA 94 anion exchange resin). The cost of the enzyme charge per pound of product produced is economical when factored over the usable biocatalyst life. However, the resin support would have to be useful and reusable, over multiple biocatalyst lives in order to justify the economical use of it in the saccharifying process of the present invention. Unfortunately, the features that make this biocatalyst an attractive option (i.e. tightness of enzyme binding to the resin, resistance to high salt concentrations and pH shifts) also make it difficult to regenerate the biocatalyst. Fortunately, a novel procedure for stripping the spent enzyme from the support has been developed. A fresh glucoamylase charge can then be successfully applied to the support.

A number of approaches to regeneration were evaluated. Initially it was hoped that bioreactor activity declined over time simply because enzyme "leaked" from the support. Regeneration would then be straightforward since fresh glucoamylase could be applied to the resin and it would be readily immobilized in the vacant resin pores. This approach was not successful because freshly applied glucoamylase did not bind well to spent biocatalyst.

It is likely that the immobilized glucoamylase is denatured over time but remains bound to the resin during the starch hydrolysis process. Some support is given to this hypothesis by the fact that the decay rate of the various biocatalysts is related to the hydrolysis operating temperature. In reality, reactor decay probably occurs through both temperature-dependent enzyme denaturation and enzyme leakage. At 45° C., enzyme denaturation appears to be the dominant factor.

It is clear that spent glucoamylase must be completely removed from the resin support so it can be effectively replaced with a fresh enzyme charge. Experiments were tried in which high concentration salt (NaCl or Na$_2$SO$_4$) solutions ($\geq$4% salt) were applied to immobilized glucoamylase reactors to displace the enzyme (See Table III below). The glucoamylase, it is to be noted, is bound to the resin not only by electrostatic attraction but also by entrapment within the pores. Thus the enzyme could not be released simply by displacement with other anions.

Another approach was to use sodium hydroxide as the stripping agent. The concept was that sodium hydroxide would chemically denature the glucoamylase and the hydroxide ions could then displace the enzyme. Both 4 weight % and 6 weight % sodium hydroxide concentrations were tested. The higher sodium hydroxide concentration was not successful as we were unable to effectively saturate the support with fresh enzyme after the 6 weight % base treatment. The 4 weight % sodium hydroxide treatment was interesting because initially it looked as though this treatment did strip off spent enzyme which could be replaced by fresh enzyme. Bioreactors regenerated in this fashion showed suitable activities for several days following regeneration (Table III). However conversion subsequently declined rapidly in these systems. Apparently some glucoamylase that was deeply bound in the resin was not being released by the 4 weight % base treatment. Heating the reactor during base treatment only intensified the problem by denaturing the glucoamylase to such an extent that it congealed in the resin (Table III).

Sulfuric acid was tested for its ability to release spent glucoamylase from the resin but again some enzyme still remained bound after such acid treatment.

The approach that finally proved effective at stripping glucoamylase from the resin support was a sequential treatment with acid (4 weight % aqueous sulfuric acid) followed by base (4 weight % aqueous sodium hydroxide). Once the resin support has been stripped of spent enzyme with this procedure, it can be efficiently loaded from a dilute glucoamylase stream exactly as if it were virgin resin. The biocatalyst shows typical activity and stability when it is regenerated in this fashion (Table III). The reason this procedure has proven so effective appears to be related to the swelling characteristics of the resin. When the acid wash is applied, the resin beads undergo a reversible expansion (20%). The acid may also serve to deglycosylate the glucoamylase, in effect making the enzyme smaller. When the base wash is then applied, enzyme is effectively denatured and displaced from the resin. The resin gradually shrinks back to the original size and free base form. It is necessary to water wash the resin support briefly between each of the treatment steps (i.e. acid to base to glucoamylase) to remove excess entrapped reagent.

At the completion of the final acid/base washing cycle, the pH of the stripped resin, in water, is in the range of about 9 to 11. Before beginning the regeneration of the resin, by the addition of fresh enzyme thereto, it is preferable to further wash the resin until the resin, in water, has a pH of about $8.0 \pm 0.5$.

bioreactor was regenerated four times, or about every 90 days. The sequential acid/base regeneration procedure was used. Despite the long term operation and frequent regenerations the physical integrity of the anion exchange resin was excellent and the level of conversion remained as expected at 93–94% with a 1.5 hours retention time. No loss or shrinkage of the resin occurred. The color, flow characteristics, and ability of the resin to bind glucoamylase was stable throughout the run. This indicates the resin has a usable lifetime of several years which will make it suitable for a continuous starch saccharification process.

In the second year of operation, the bioreactor was used to determine the proper interval between regenerations. After six months of operation at 45° C. the conversion had dropped to 92.5%, demonstrating that a regeneration frequency of less than twice a year would

TABLE III

REGENERATION PROCEDURES ATTEMPTED

| Example | Stripping Agent Used | Enzyme loading[1] | Conversion[2] Day 1 | Day 10 |
|---|---|---|---|---|
| 9 | None | 400 IU/ml (RT = 2 hr) | 93 | 75 |
| 9 | None | 400 IU/ml (RT = 1 hr) | 92 | 73 |
| 9 | 2% Sodium Chloride | 600 IU/ml (Batch) | 93 | 87 |
| 9 | 4% Sulfuric Acid | 400 IU/ml (RT = 1 hr) | 94 | 80 |
| 9 | 6% Sodium Hydroxide (60 C) | 250 IU/ml (RT = 0.5 hr) | 86 | 79 |
| 9 | 4% Sodium Hydroxide | 500 IU/ml (RT = 1 hr) | 94 | 88 (4 days) |
| 9 | 4% Sulfuric Acid | 600 IU/ml (RT = 1 hr) | 93 | 93 |
|   | 4% Sodium Hydroxide |   |   |   |
| 9 | 4% Sulfuric Acid | 500 IU/ml (RT = 1 hr) | 94 | 92 |
|   | 4% Sodium Hydroxide |   |   |   |
| 10 | 4% Sulfuric Acid | 100 IU/ml (RT = 1 hr) | 93 | 92 (102 days) |
|   | 4% Sodium Hydroxide |   |   |   |

[1] As per procedure used in Example 1 above.
[2] Conversions obtained when regenerated catalyst was used to hydrolyze maltodextrin to glucose.

EXAMPLE 10

A long term run was conducted to verify that the rather harsh regeneration process of the present invention described above will not cause premature deterioration of the anion exchange resin. The standard feed of 2 weight % maltodextrin (M-200) and a 0.75 hour residence time were used during the first 102 days of the run, and at a residence time of 1.5 hours for the next 266 days. During this first year of operation, the frequency of regeneration was deliberately increased so that the bioreactor was finally shut down after 29 months of operation and nine regenerations. At the time it was shutdown, the conversion was 93.5% demonstrating economic use of the resin support.

For the purposes of recoverying, stripping and regenerating the depleted biocatalyst during the long term continuous operation of the starch hydrolysis process in the column bioreactor, the bioreactor is shut down completely for a short period of time, of about 5 days, to effect such regeneration and recharging of the regenerated biocatalyst.

| Comparison With Teachings of French Patent 2372653 | |
|---|---|
| Example 1 French Patent Batch Loading Process | Example 2 above Present Invention Continuous Loading Process |
| (1) Amberlite IRA-93 Resin used and washed with water | (1) Amberlite IRA-94 Resin used and washed with water |
| (2) Novo 150L glucoamylase enzyme used | (2) Novo 200L glycoamylase enzyme used |
| (3) resin balanced with 0.01 M Na acetate at pH4 | (3) not used |
| (4) Resin filtered and dried (or not) under 17.5 mm Hg vacuum | (4) not used |
| (5) Resin moistened or contracted in batch mode of operation with a solution of enzyme. Enzyme solution buffered with 0.01 M Na acetate pH 4.0 | (5) 5 volumes of enxyme solution fed per volume of resin in a continuous mode of operation. Enzyme solution buffered with 0.05 M Na acetate-pH 4.3 |
| (6) adsorption at 4° C. over 12 hours | (6) adsorption at 45° C. over 5 hours |
| (7) Maximum fixed loading up to 0.25 ml of enzyme per gram dry resin (800 IU/gm) | (7) Maximum fixed loading up to 1100 to 1500 IU/gm dry resin |
| (8) after loading the resin | (8) omitted |

| Comparison With Teachings of French Patent 2372653 | |
|---|---|
| Example 1<br>French Patent<br>Batch Loading Process | Example 2 above<br>Present Invention<br>Continuous Loading Process |
| supported enzyme is washed repeatedly under agitation for 30 minutes at 20° C. with buffer at a ratio of 20 ml solution per gram of dry resin | |
| (9) Percent of fed enzyme absorbed to give a catalyst of maximum fixed activity = 33% | (9) Percent of fed enzyme absorbed to give a catalyst of maximum fixed activity = 75%. |

The enzyme loading process of the present invention thus provides significantly higher loading efficiencies, under significantly better loading conditions of time and temperature, with a much more simplified process.

| Starch Hydrolysis<br>Example 4 of French Patent | Starch Hydrolysis Example 6<br>of the Present Invention |
|---|---|
| (10) 40° C. | (10) 45° C.-at this higher temperature microorganism contamination is minimized |
| (11) pH 4.0 | (11) pH 4.0 |
| (12) retention time of 0.83 hours | (12) retention time of 0.75 hrs.<br>-at a retention time of 0.83 hours the % conversion is 91.7% |
| (13) % conversion = 80 | (13) % conversion = 91% |
| (14) length of run = 30 days | (14) length of run = 90 days |
| (15) maltodextrin solution used = 250 gr/l | (15) maltodextrin solution used = 220 gr/l |

Thus, when the biocatalysts made by the process of the present invention are used in the hydrolysis of maltodextrin, they provide significantly higher % conversions under the respective operating conditions suggested for the two biocatalyst systems.

What is claimed is:

1. A process for preparing a biocatalyst comprising glucoamylase enzyme immobilized on porous, particulate, macroreticular anionic exchange resin, said glucoamylase being a water soluble fungal derived enzyme, and said resin being in free base form and having a particle size of about 0.50±0.20 mm and said particles having pore sizes therein of about 900 to 2000 Angstrom units, which comprises depositing said enzyme on said resin in a continuous deposition mode of operation, said depositing being carried out in a period of about 1 to 2 hours at a temperature not to exceed 50° C. with 10±5 volumes of enzyme solution per volume of said resin, said enzyme solution having a concentration of about 100 to 200 IU of said enzyme per ml of said solution and said solution being buffered with acetate buffer at a pH of 4.0±0.3, and said depositing thereby providing a loading of about 1000 to 1500 IU of said enzyme per gram of said resin in dry form, and stabilizing the resultant deposited enzyme by treating the deposited enzyme with an aqueous solution of carbohydrate selected from the group consisting of starch, glucose and oligosaccharides in such an amount and for such a period of time as to render said enzyme substantially non-leachable from said resin when the resin is in an expanded or non-expanded ionic form.

2. A process in claim 1 in which said resin is a crosslinked styrene-divinyl benzene resin.

3. A process as in claim 2 in which said resin is a weak base ion exchange resin.

4. A process as in claim 1 in which said biocatalyst is disinfected with an antibiotic which is inactivated at 45° C. or higher.

5. A process as in claim 4 in which said antibiotic is nystatin.

6. A process as in claim 1 which further comprises treating the enzyme deposited resin with a dilute aqueous solution of a salt of a strong acid and a strong base in such quantities and for such period of time as to remove therefrom any significant quantities of microbial inhibitors therein.

7. A process as in claim 5 in which said salt is sodium sulfate.

8. A process as in claim 1 in which said oligosaccharide is dextrin.

9. A process as in claim 5 in which said salt is sodium sulfate.

10. A multi-step process for preparing, stabilizing, using, regenerating and reusing a biocatalyst comprising glucoamylase enzyme immobilized on porous, particulate, macroreticular anionic exchange resin, said glucoamylase being a water soluble fungal derived enzyme, and said resin being in free base form and having a particle size of about 0.50±0.20 mm and said particles having pore sizes therein of about 900 to 2000 Angstrom units, which comprises (a) preparing said biocatalyst by depositing said enzyme on said resin in a contonuous deposition mode of operation, said depositing being carried out in a period of about 1 to 2 hours at a temperature not to exceed 50° C. with 10±5 volumes of enzyme solution per volume of said resin, said enzyme solution having a concentration of about 100 to 200 IU of said enzyme per ml of said solution and said solution being buffered with acetate buffer at a pH of 4.0±0.3, and said depositing thereby providing a loading of about 1000 to 1500 IU of said enzyme per gram of said resin in dry form, (b) stabilizing said biocatalyst by treating the deposited enzyme with an aqueous solution of carbohydrate selected from the group consisting of starch, glucose and oligosaccharides in such an amount and for such a period of time as to render said enzyme substantially non-leachable from said resin when the resin is in an expanded or non-expanded ionic form, (c) using the biocatalyst to saccharify a liquified starch at 45° C. or higher until the biocatalyst reaches an undesired low level of bioactivity for this purpose, (d) recovering such low activity biocatalyst from said liquified starch, (e) stripping the enzyme from said low activity biocatalyst by sequentially treating the supported enzyme with, as the sole stripping treatment, at least one cyclic treatment of first with strong acid and then with strong base, (f) adjusting the pH of the stripped resin, in water, to 8.0±0.5, and then sequentially repeating at least once the combination of at least said steps (a), (b) and (c).

11. A process as in claim 10 in which said resin is a crosslinked styrene-divinyl benzene resin.

12. A process as in claim 11 in which said resin is a weak base ion exchange resin.

13. A process as in claim 10 in which said biocatalyst is disinfected with an antibiotic which is inactivated at 45° C. or higher, between said steps (a) and (b).

14. A process as in claim 13 in which said antibiotic is nystatin.

15. A process as in claim 10 which further comprises treating the biocatalyst produced in said step (b) with a dilute aqueous solution of a salt of a strong acid and a strong base in such quantities and for such period of time as to remove therefrom any significant quantities of microbial inhibitors therein.

16. A process as in claim 10 in which said oligosaccharide is dextrin.

* * * * *